United States Patent
Tang et al.

(10) Patent No.: US 8,101,101 B2
(45) Date of Patent: Jan. 24, 2012

(54) METHODS FOR IMPROVING THE RESISTANCE OF FUMIGANT SORPTION IN A PRODUCE CONTAINER AND A RELATED PRODUCE CONTAINERS

(75) Inventors: Jiansheng Tang, Mars, PA (US); Jeffory E. Russell, Sewickley, PA (US); Christine Hetzer, Monaca, PA (US); David A. Cowan, Cranberry Township, PA (US)

(73) Assignee: NOVA Chemicals Inc., Moon Township, PA (US)

( * ) Notice: Subject to any disclaimer, the term of this patent is extended or adjusted under 35 U.S.C. 154(b) by 853 days.

(21) Appl. No.: 11/633,202

(22) Filed: Dec. 4, 2006

(65) Prior Publication Data
US 2007/0148385 A1 Jun. 28, 2007

Related U.S. Application Data

(60) Provisional application No. 60/753,168, filed on Dec. 22, 2005.

(51) Int. Cl.
*B32B 37/00* (2006.01)
*A23B 4/16* (2006.01)
*B29D 22/00* (2006.01)
*C08J 9/00* (2006.01)

(52) U.S. Cl. .......... 264/45.4; 264/25; 521/50; 428/35.7; 426/316

(58) Field of Classification Search ................. 264/45.4, 264/25; 521/50; 428/35.7; 426/316
See application file for complete search history.

(56) References Cited

U.S. PATENT DOCUMENTS

| | | | |
|---|---|---|---|
| 2,656,334 A | 10/1953 | D'Alelio |
| 2,983,692 A | 5/1961 | D'Alelio |
| 3,023,175 A | 2/1962 | Rodman, Jr. |
| 3,817,965 A | 6/1974 | Mace et al. |
| 3,968,879 A | 7/1976 | Lucas, Sr. et al. |
| 4,781,983 A | 11/1988 | Stickley |
| 5,016,777 A | 5/1991 | Marvin |

(Continued)

FOREIGN PATENT DOCUMENTS

EP 0 488 040 A2 11/1991

(Continued)

OTHER PUBLICATIONS

Gamliel et al., 1998 A. Gamliel, A. Grinstein, L. Klien, Y. Cohen and J. Katan, Permeability of plastic films to methyl bromide: field study, Crop Prot. 17 (3) (1998), pp. 241-248.*

*Primary Examiner* — Christina Johnson
*Assistant Examiner* — Michael Piery
(74) *Attorney, Agent, or Firm* — Gary F. Matz

(57) ABSTRACT

Methods for improving the resistance of fumigant sorption in produce containers made from expandable polystyrene particles in a fumigation process, and related produce containers. An embodiment involves pre-expanding the expandable polystyrene particles to form pre-expanded particles; applying a coating comprised of a chemical selected from the group consisting of mineral oil, polyethylene wax, ethylene vinyl alcohol copolymer, and polyethylene glycol to the pre-expanded particles and in amount of 0.05 to 5.0 parts per hundred; and forming the container from the pre-expanded particles. A further embodiment involves applying the chemical coating to the expandable particles; pre-expanding the expandable polystyrene particles to form pre-expanded particles; and forming the containers from the pre-expanded particles. Other methods involve increasing the cell size of the expandable particles used to form the produce container.

11 Claims, 1 Drawing Sheet

U.S. PATENT DOCUMENTS

| | | | |
|---|---|---|---|
| 5,064,716 A * | 11/1991 | Chou et al. | 428/336 |
| 5,162,381 A | 11/1992 | Richard et al. | |
| 5,318,789 A * | 6/1994 | Nakagawa et al. | 426/316 |
| 5,690,272 A | 11/1997 | England | |
| 6,127,439 A | 10/2000 | Berghmans et al. | |
| 6,160,027 A | 12/2000 | Crevecoeur et al. | |
| 6,242,540 B1 | 6/2001 | Crevecoeur et al. | |
| 6,506,807 B1 | 1/2003 | Yanagihara et al. | |
| 2002/0117769 A1 | 8/2002 | Arch et al. | |
| 2004/0121101 A1 * | 6/2004 | Tang et al. | 428/36.5 |
| 2004/0210056 A1 | 10/2004 | Wood et al. | |

FOREIGN PATENT DOCUMENTS

| | | |
|---|---|---|
| GB | 1 409 285 | 10/1975 |

\* cited by examiner

METHODS FOR IMPROVING THE RESISTANCE OF FUMIGANT SORPTION IN A PRODUCE CONTAINER AND A RELATED PRODUCE CONTAINERS

CROSS REFERENCE TO RELATED PATENT APPLICATION

The present non-provisional patent application is entitled to and claims, under 35 U.S.C. §119(e), the benefit of U.S. Provisional Patent Application No. 60/753,168, filed Dec. 22, 2005, which is hereby incorporated herein in its entirety by reference.

BACKGROUND OF THE INVENTION

1. Field of the Invention

The present invention relates to produce containers made from expandable polymer particles, e.g. expandable polystyrene particles (EPS), and to methods for improving the resistance of fumigant, e.g. methyl bromide, sorption in the produce containers in a fumigation process.

2. Background Art

Fumigants are used to eradicate pests from containers for the international shipment of produce, e.g. fruits, e.g. grapes, and vegetables, e.g. tomatoes. In general, the fumigation process is necessary when produce is either imported or exported in order to control the infestations of pests, e.g. Mediterranean fruit fly. A commonly used fumigant is methyl bromide, which is highly toxic.

The types of containers most commonly used for shipping produce are made of wood, paperboard, or plastic materials, e.g. expandable polymer particles, e.g. expandable polystyrene particles. Wooden containers need to be extremely inexpensive and yet sturdy and the cost of wood has become exorbitant. Cardboard or paperboard containers tend to collapse when a number of filled containers are stacked on top of each other. A container made of expandable polystyrene particles provides the sturdiness needed to support the number of filled containers when stacked on top of each other and is relatively inexpensive compared to wooden containers. Examples of containers made from expandable polystyrene particles in a molding process are disclosed in U.S. Pat. No. 5,016,777 issued to Morley Marvin on May 21, 1991 and in U.S. Pat. No. 5,690,272 issued to James England on Nov. 25, 1997. The latter patent discloses a container that is hand assembled and is suitable for shipping produce.

However, due to the nature of foamed polymer, particularly foamed polystyrene, in that it contains open cells or voids, produce containers made of these particles have a relatively high level of fumigant absorption rate compared to produce containers made of wood or paperboard. Additionally, the fumigant tends to remain desorbed in the walls of the container made of expandable polymer particles for a long period of time after the fumigation process.

When produce is imported into or exported from a country, the general procedure is to stack two or more rows of containers containing the vegetables or fruits onto a pallet, and then transport the pallet into a fumigation chamber. The fumigant, which typically is methyl bromide, is delivered into the chamber for two hours in order to kill the infestation that may be present, and then to interrupt the delivery of the fumigant for the next two hours so that the methyl bromide can dissipate before the chamber can be safely opened to remove the pallet and containers.

The United States Department of Agriculture (USDA) requires that the fumigation process meet the following criteria: 1) The methyl bromide concentration in the fumigation chamber during the fumigation process should not be lower than the minimum concentration required by USDA schedule T101-I-2-1, e.g. 48 ounces/1000 feet$^3$ for the first half hour and 38 ounces/1000 feet$^3$ for 2.0 hours, at a temperature between 40-49° F. (Table 1). 2) The residual methyl bromide concentration should not be more than 5 ppm after degassing, i.e. removing the methyl bromide from the chamber.

Studies have shown that current produce containers made of expandable polystyrene particles cannot maintain the mandated minimum methyl bromide concentrations during the fumigation process when the initial concentration required by USDA, e.g. 64 ounces/1000 feet$^3$ at 40° to 49° F., is applied because these containers absorb a great amount of methyl bromide. Data also show that these containers have a high residual concentration (higher than the threshold limit value (TLV) of 5 ppm) after a typical aeration process following the fumigation process.

Therefore, the produce market requires improved expandable polymer containers that absorb and retain less fumigant during the fumigation process.

There is also a need to provide a method for improving the resistance of fumigant, e.g. methyl bromide, sorption in a produce container made from expandable polymer particles.

SUMMARY OF THE INVENTION

The invention has met the above needs. The present invention provides a method for improving the resistance of fumigant sorption in a produce container made from expandable polymer particles in a fumigation process. This method involves the steps comprising: applying to the expandable polystyrene particles a coating comprised of a chemical selected from the group consisting of mineral oil, polyethylene wax, ethylene vinyl alcohol copolymer, and polyethylene glycol in an amount ranging from about 0.05 to about 5.0 parts per hundred; pre-expanding the expandable polystyrene particles to form pre-expanded particles with a density ranging from about 12.0 to about 1.0 pounds per cubic feet to form pre-expanded particles; and forming a produce container from the pre-expanded particles. The chemicals may be selected from the group consisting of polyethylene glycol, ethylene vinyl alcohol copolymer, polyethylene wax, and mineral oil. Preferably, the chemical is ethylene vinyl alcohol copolymer or mineral oil.

A further embodiment of the present invention provides a method for improving the resistance of fumigant sorption in a produce container made from expandable polystyrene particles in a fumigation process, the steps comprising increasing the cell size of the expandable polystyrene particles; and using the expandable polystyrene particles with an increased cell size to mold a produce container.

Further embodiments of the invention provide produce containers obtained by the methods of the invention.

These and other aspects of the invention will be more fully appreciated and understood from the following description and the appended claims.

DETAILED DESCRIPTION OF THE INVENTION

Figure 1:
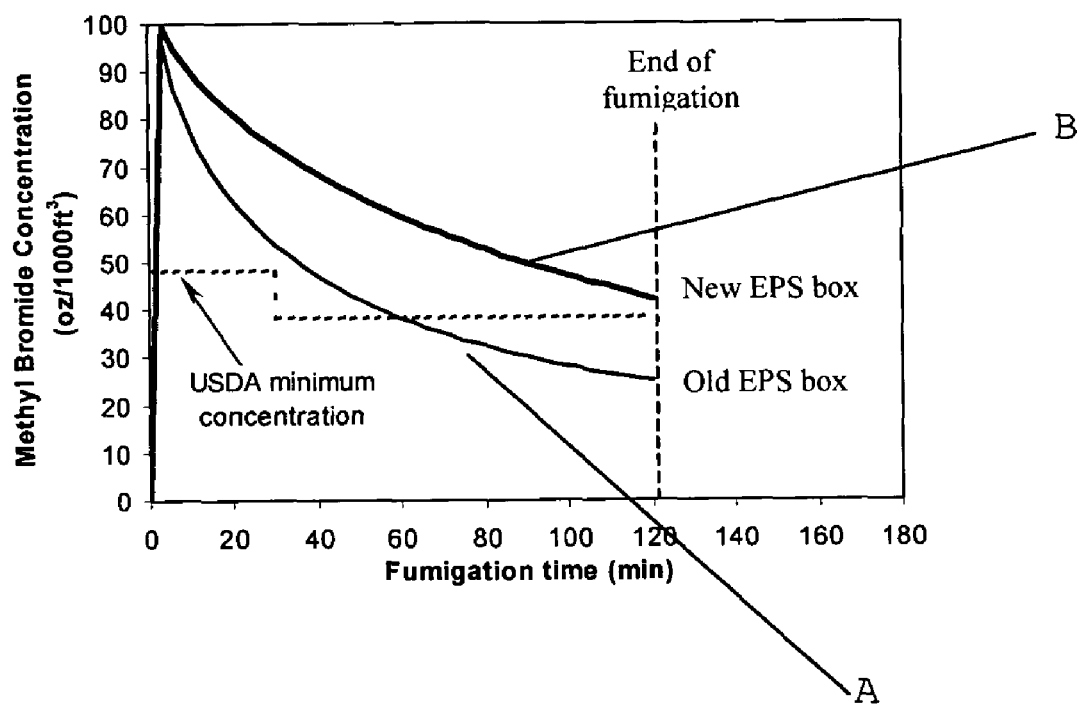
FIG. 1 is a graph showing the methyl bromide concentrations (ounces/1000 feet$^3$) versus fumigation time (minutes) for the USDA minimum requirement for the present (old) EPS containers indicated at "A" and for the inventive (new) EPS containers indicated at "B".

The present inventors have found a solution to providing produce containers, made from expandable polymer particles, particularly polystyrene particles, with improved resistance to methyl bromide in the fumigation process. The findings were:

1. Methyl bromide sorption in produce containers is dependent on the volume of the container material, i.e. less EPS foam volume results in less methyl bromide sorption.
2. Thin-wall produce containers, which use less EPS foam material is favorable in the fumigation process.
3. Methyl bromide is mainly absorbed by the cells of the EPS foam material, and therefore, a larger cell size would decrease the amount of foam material and also would decrease the methyl bromide absorption.
4. A relatively thick skin on the expandable polymer particles would tend to retard the penetration of methyl bromide into the produce container.
5. A surface modification of EPS particles using polyethylene wax and/or mineral oil decreases methyl bromide sorption in EPS produce containers.
6. Gas barrier material, e.g. ethylene vinyl alcohol (EVOH), incorporated into the EPS particles tends to decrease the sorption of methyl bromide in EPS produce containers.

The produce container of the invention is molded from expandable polymer particles, which may be made from any suitable homopolymer or copolymer. Particularly suitable are homopolymers derived from vinyl aromatic monomers including styrene, isopropylstyrene, alpha-methylstyrene, nuclear methylstyrenes, chlorostyrene, tert-butylstyrene, and the like, as well as copolymers prepared by the copolymerization of at least one vinyl aromatic monomer with monomers such as divinylbenzene, butadiene, alkyl methacrylates, alkyl acrylates, acrylonitrile, and maleic anhydride, wherein the vinyl aromatic monomer is present in at least 50% by weight of the copolymer.

In most embodiments, styrenic polymers are preferred, particularly polystyrene. However, other suitable polymers may be used, such as polyolefins (e.g. polyethylene, polypropylene), and polycarbonates, polyphenylene oxides, and mixtures thereof. Preferably, in the embodiments the expandable polymer particles are expandable polystyrene (EPS) particles.

The particles may be in the form of beads, granules, or other particles convenient for expansion and molding operations. Particles polymerized in an aqueous suspension process are essentially spherical and are preferred for molding the foam containers of the invention.

The expandable polystyrene particles are impregnated with a suitable blowing agent using any conventional method. For example, the impregnation can be achieved by adding the blowing agent to the aqueous suspension during the polymerization of the polymer, or alternatively by re-suspending the polymer particles in an aqueous medium and then incorporating the blowing agent as taught in U.S. Pat. No. 2,983,692 to D. Alelio.

Any gaseous material or material which will produce gases on heating can be used as the blowing agent. Conventional blowing agents include aliphatic hydrocarbons containing 4 to 6 carbon atoms in the molecule, such as butanes, pentanes, hexanes, and the halogenated hydrocarbons, e.g. CFC's and HCFC's, which boil at a temperature below the softening point of the chosen polymer. Mixtures of the aliphatic hydrocarbons blowing agents can also be used.

Alternatively, water can be blended with these aliphatic hydrocarbons blowing agents or water can be used as the sole blowing agent as taught in U.S. Pat. Nos. 6,127,439; 6,160,027; and 6,242,540 assigned to NOVA Chemicals (International) S.A. In the aforesaid patents, water-retaining agents are used. The weight percentage of water for use as the blowing agent can range from 1 to 20%. The teachings of U.S. Pat. Nos. 6,127,439, 6,160,027 and 6,242,540 in their entirety are incorporated herein by reference.

The manufacture of molded foam containers, e.g. produce containers for shipping produce, e.g. fruits e.g. grapes and vegetables, e.g. tomatoes, from polymer particles, particularly expandable polystyrene (EPS) particles, is well known.

Typically, the polystyrene beads or particles are impregnated with a hydrocarbon, e.g. pentane, as a blowing agent, which boils below the softening point of the polystyrene thereby causing the particles to expand when heated. The amount of blowing agent impregnated in the polymer may range from about 2.0 to about 10.0 weight percent.

The expandable polystyrene particles may be obtained by polymerization, and the blowing agent may be incorporated into the polymer before, during, or after the polymerization process. A preferred polymerization process for the production of expandable polystyrene particles is suspension polymerization.

A preferred polymerization process for the production of expandable particles is suspension polymerization. In this process, a polymer composition is polymerized in an aqueous suspension in the presence of from 0.1 to 1.0% by weight of a free radical initiator and the blowing agent.

For the suspension polymerization many methods and initiators are known to those skilled in the art. In this respect reference is made to e.g., U.S. Pat. Nos. 2,656,334 and 3,817,965 and European Patent Application No. 488,040. The initiators disclosed in these references can also be used to make the expandable particles that in turn are used to make the foamed cellular particles of the present invention. Suitable initiators are organic peroxy compounds, such as peroxides, peroxy carbonates and peresters. Typical examples of these peroxy compounds are $C_{6-20}$ acyl peroxides, such as decanoyl peroxide, benzoyl peroxide, octanoyl peroxide, stearyl peroxide, peresters, such as t-butyl perbenzoate, t-butyl peracetate, t-butyl perisobutyrate, t-butylperoxy 2-ethylhexyl carbonate, carbonoperoxoic acid, OO-(1,1-dimethylpropyl) O-(2-ethylhexyl) ester, hydroperoxides and dihydrocarbyl peroxides, such as those containing $C_{3-10}$ hydrocarbyl moieties, including di-isopropyl benzene hydroperoxide, di-t-butyl peroxide, dicumyl peroxide or combinations thereof. Other initiators, different from peroxy compounds, are also possible, as for example α,α'-azobisisobutyronitrile.

The suspension polymerization is carried out in the presence of suspension stabilizers. Suitable suspension stabilizers are well known in the art and comprise organic stabilizers, such as poly (vinyl alcohol), gelatine, agar, polyvinyl pyrrolidine, polyacrylamide; inorganic stabilizers, such as alumina, bentonite, magnesium silicate; surfactants, such as sodium dodecyl benzene sulfonate; or phosphates, like tricalciumphosphate, disodium-hydrogen phosphate, optionally in combination with any of the stabilizing compounds mentioned earlier. The amount of stabilizer may suitably vary from 0.001 to 0.9% by weight, based on the weight of the aqueous phase.

The expandable particles may also contain an anti-static additive; a flame retardant; a colorant or dye; a filler material, such as carbon black, titanium dioxide, aluminum, and graphite, which are generally used to reduce thermal conductivity; stabilizers; and plasticizers, such as white oil or mineral oil. The particles may suitably be coated with coating compositions comprised of white oil or mineral oil, silicones, metal or glycerol carboxylates, suitable carboxylates being glycerol mono-, di- and tri-stearate, zinc stearate, calcium stearate, and magnesium stearate; and mixtures thereof. Examples of such compositions have been disclosed in GB Patent No. 1,409,285 and in Stickley U.S. Pat. No. 4,781,983.

In the invention, the formation of molded containers from impregnated polystyrene particles is generally done in two steps. First, the impregnated raw particles having a density of about 40.0 to 32.0 pounds per cubic foot are pre-expanded to a density of from about 1.0 to about 12.0 pounds per cubic foot. Second, the pre-expanded particles ("pre-puff") are heated in a closed mold to further expand the pre-expanded particles to fuse the beads together to form a foam article, e.g. produce containers, having the shape of the mold.

The pre-expansion step is conventionally carried out by heating the impregnated beads via any conventional heating medium, such as steam, hot air, hot water, or radiant heat. One generally accepted method for pre-expanding impregnated thermoplastic particles is taught in U.S. Pat. No. 3,023,175 to Rodman.

In some embodiments, expandable polystyrene particles may be foamed cellular polymer particles as taught in Arch et al. U.S. patent application Ser. No. 10/021,716 assigned to NOVA Chemicals Inc, the teachings of which in their entirety are incorporated herein by reference. The foamed cellular polystyrene are pre-expanded to a density of from about 12.5 to about 34.3 pounds per cubic foot, and contain a volatile blowing agent level less than 6.0 weight percent, preferably from about 2.0 wt % to about 5.0 wt %, and more preferably ranging from about 2.5 wt % to about 3.5 wt % based on the weight of the polymer.

As stated herein above, the expandable polystyrene particles used to make foam containers are generally prepared by an aqueous suspension polymerization process, which results in particles that can be screened to relatively precise particle sizes. Typically, the raw particle diameters for making containers may range from about 0.01 to about 0.15 inch. It has been known to produce cups from beads having a diameter of about 0.035 inch. Typically, these raw particles, which are expandable, i.e. not expanded, have a density ranging from about 40.0 to about 32.0 pounds per cubic feet.

In an embodiment of the invention, a method of improving the resistance of fumigant sorption in a produce container made from expandable polystyrene particles in a fumigation process, involves the steps of starting with expandable particles, i.e. not expanded, having a density ranging from about 40.0 to about 32.0 pounds per cubic feet, and pre-expanding the expandable polystyrene particles to a density ranging from about 12.0 pounds per cubic feet to about 1.0 pounds per cubic feet to form pre-expanded particles, applying a chemical to the pre-expanded particles to coat the particles, and then injecting these coated particles into a mold having the shape of a produce container.

The chemical which is applied to the pre-expanded particles is selected from the group consisting of mineral oil, polyethylene wax, ethylene vinyl alcohol copolymer, and polyethylene glycol (PEG), and combinations thereof, in an amount ranging from about 0.05 to about 5.0 parts per hundred (ppm).

Suitable polyethylene waxes have a molecular weight ranging from about 500 to about 2500. Suitable polyethylene glycols have a molecular weight ranging from about 250 to about 80. Suitable mineral oils are available under the trade name PENRECO® and DRAKEOL®. Suitable mineral oils obtained under the trade mark DRAKEOL® include DRAKEOL® 19, 21, 25, 32, 33, 34, 35, 350, 357, and 400 series. Suitable ethylene vinyl alcohol copolymers are copolymers having an ethylene content varying from about 29% to about 40% by weight; pre-prepared in 50/50 water/isopropyl solution with concentrations ranging from 2.5 wt % to 20 wt %, e.g., SOARNOL grades E3808, ET 3803, DT 2903, A4412.

Preferably, the chemical is mineral oil or ethylene vinyl alcohol copolymer, and preferably, the amount applied to the particles ranges from 0.10 to about 1.0 parts per hundred.

The chemical may be applied to the pre-expanded particles through one of the various methods available, which include brushing, spraying, or dipping the pre-expanded particles into a solution of the chemical, or dry blending of the chemical with the pre-expanded particles. A chemical solution consists of a concentration of 2.5%-20% of about 50% weight percent isopropyl alcohol and about 50% weight percent water. The chemical may be coated onto the pre-expanded particles.

The coating preferably is applied to the pre-expanded particles, but may also be applied to the outer and the inner surfaces of the produce container.

In a further embodiment, the invention provides a method of improving the resistance of fumigant sorption in a produce container made from expandable polystyrenes particles in a fumigation process, where the steps comprise applying a chemical to the expandable (not expanded) polystyrene particles, pre-expanding the expandable polystyrene particles to a density ranging from about 12.0 to about 1.0 pounds per cubic feet to form pre-expanded or pre-puff particles, and then injecting these pre-expanded particles into a mold having the shape of a produce container.

Generally, the expandable particles have a density ranging from about 40.0 to about 32.0 pounds per cubic feet. The chemical will be selected from the group consisting of mineral oil, polyethylene wax, ethylene vinyl alcohol copolymer, and polyethylene glycol (PEG) and combinations thereof, in an amount ranging from about 0.05 to about 5.0 parts per hundred. Preferably the chemical is either mineral oil or ethylene vinyl alcohol copolymer, and the amount applied to the expandable polystyrene particles ranges preferably from about 0.1 to about 1.0 parts per hundred.

The chemical may be applied to the expandable particles through one of the various methods available, which include brushing, spraying, or dipping the expandable particles into a solution of the chemical, or dry blending of the chemical with the expandable particles. A chemical solution consists of concentrations 2.5% to 20% of about 50% weight percent isopropyl alcohol and about 50% weight percent water. The chemical may form a coating on the expandable particles.

The coating preferably is applied to the expandable particles, but may also be applied to the outer and the inner surfaces of the produce container.

The chemical applied to the expandable or pre-expanded particles may be dried by directing a stream of hot air at a temperature range of ambient to about 100° C., preferably 50° C., onto the surface of the particles.

The greater the coating load, the thicker the coating layer, the better the resistance to fumigant sorption, and the longer the drying time for the coating on the surface of the particles or produce container.

A further embodiment of the invention involves a method of improving the resistance of fumigant sorption in a produce container made from expandable polystyrene particles by increasing the cell size of the expandable polystyrene particles, and then injecting these particles in a mold having the shape of a produce container.

The drying process for expandable particles typically involves directing a stream of hot air at a temperature range of 70° C. to about 110° C., preferably 80° C. to 100° C., onto the surface of the expandable polystyrene particles for about 1 minute to about 60 minutes.

The present invention is further illustrated in the following examples; however, without restricting its scope.

EXAMPLES

In the examples, a prototype chamber testing method for measuring methyl bromide sorption was devised which employs a simple chamber set-up and an effective data analysis model to precisely and conveniently evaluate the fumigant sorption in molded expandable polystyrene particles.

An open testing chamber was set up and consisted of a rectangular stainless steel container with a specific volume of either 2.0 cubit feet. A flat stainless steel cover was placed on top of the chamber and sealed with a strip of caulking for a gas-tight fit. Methyl bromide gas was introduced into the chamber by a gas-tight syringe with an aliquot, which gas was taken from a bag made from TEDLAR® (E.I. DuPont DeNemours & Company) films or sheets of polymers of vinyl fluoride. The bag was first filled with pure gas obtained from a cylinder of standard fumigation grade methyl bromide.

The sealed testing chamber was placed in a small cubical area equipped with an air conditioner for controlling the external temperature of the produce container to a temperature of about 45° F. while the testing chamber was injected with the methyl bromide gas at a dosage rate of about 4.0 pounds per 1000 cubic feet. The gas in the chamber was sampled with a portable gas chromatograph, which was calibrated with methyl bromide.

Data was collected every 180 seconds over a four hour period. The first two-hour period is the static exposure period where the produce container is exposed to methyl bromide at the initial dosage rate of about 4.0 pounds per cubic feet. The second two-hour period is referred to as the dynamic aeration period. During this time, an external pump is actuated to introduce aeration air into the chamber, which exchanges the methyl bromide gas for clean air in the chamber at a rate of 2 to 3 air volumes per minute. Data were collected during this time frame as well. The allowed maximum concentration of the methyl bromide gas in the chamber at the end of this second two-hour period (aeration) was 5 parts per million.

Example 1

Increased Cell Size

In order to obtain a larger cell size in the polystyrene particles, polyethylene wax, which is usually used in the polymerization process as a nucleating agent to reduce the cell size, was eliminated from the formulation for the synthesis of NOVA D240B beads (NOVA Chemicals Inc.). As a comparison, normal polystyrene particles (NOVA D240 beads) were also synthesized or formulated with polyethylene wax as a nucleating agent. The polymerization process was done in the lab in a pilot plant scale following typical suspension polymerization process. The synthesized expandable polystyrene beads were pre-expanded in a Hirsch batch pre-expander to a 2.5-pcf density and then were aged for 24 hours before molding. EPS grape boxes were molded from aged pre-puff using a KG 606 or Kurtz 812 molding machine. The dimensions of the grape box were 20×16×6.75 inches. Grape boxes with wall thickness of 1 inch were molded to evaluate the methyl bromide sorption.

The molded EPS grape boxes were tested for methyl bromide sorption using the following method:

One EPS grape box was placed inside the testing chamber, which was sealed with a flat cover by applying strip caulking around the lip of the chamber to ensure the chamber was gas-tight.

Methyl bromide gas was introduced into the chamber by a gas-tight syringe, with the aliquot taken from the TEDLAR® bag filled with pure gas. The pure gas initially obtained from a cylinder of standard fumigation grade methyl bromide.

The amount of gas injected into the chamber was determined by the USDA (United States Daily Allowance) Treatment Manual, Interim Edition, published by Plant Protection Quarantine of APHIS (Animal and Plant Health Inspection Service). The recommendations in this manual are based on uses authorized under provisions of FIFRA (Federal Insecticide, Fungicide, and Rodenticide Act). The amount of gas injected was dependent on the commodity and the temperature of the commodity, which are listed in the treatment schedules in the Treatment Manual, as represented in Table 1.

The air conditioner maintained the environmental temperature at the specific levels shown in Table 1. Here, a 45° F. temperature and the corresponding dosage were used. After the gas was injected, the gas in the chamber was sampled with the portable gas chromatograph. Data were collected every 180 seconds over 4 hours. The minimum USDA concentrations levels for phytotoxicity are based on the first two hours of exposure. The dynamic aeration period concentrations are important for worker and environmental exposure considerations.

TABLE 1

USDA Fumigation Protocol
Grapes from Chile/External Feeders/Insects other than
Mediterranean Fruit Fly or Vine Moth

| Temperature | Dosage Rate lb/1000 ft$^3$ | Minimum Concentration (oz/1000 ft$^3$) | |
|---|---|---|---|
| | | 0.5 hr (80%) | 2 hrs (60%) |
| 80 F. or above | 1.5 | 19 | 14 |
| 70-79 F. | 2.0 | 26 | 19 |
| 60-69 F. | 2.5 | 32 | 24 |
| 50-59 F. | 3.0 | 38 | 29 |
| 40-49 F. | 4.0 | 48 | 38 |

Ref: USDA PPQ Treatment Schedules T101-i-2/T101-i-2-1

The methyl bromide sorption rate during the first 2 hours exposure period is calculated using the following equation:

$$\text{MeBr sorption rate} = 1 - C_2/C_0$$

where $C_2$ is the methyl bromide concentration at the end of the two-hour methyl bromide exposure period, and $C_0$ is the initial methyl bromide concentration of the exposure period.

The methyl bromide sorption rate at the end of the two-hour exposure period was used here to compare the sorption ability of different grape boxes at the specific test conditions (same test chamber, same number of grape box tested, and same dosage of methyl bromide used, etc.).

The test results show that the methyl bromide sorption rate of the EPS grape box with the normal cell size was 55% while the grape box of the invention with the larger cell size (nucleation agent removed) was 40%. The increase in cell size (removal of polyethylene wax nucleation agent) significantly decreases the methyl bromide sorption of the EPS grape boxes.

Example 2

Particle Coating I

NOVA D240B polystyrene raw beads were lubed using the following formulation and process:

D240B: 400 lbs
Pluracol E400 PEG: 1500 ppm based on the weight of the D240B polystyrene particles
Blend the above two materials for 20 minutes
Petrolite 5000 T6 polymer: 2500 ppm based on the weight of the D240B beads.
Blend the above materials for another 20 minutes.

The pre-expansion and molding process of Example 1 was repeated to make EPS grape boxes. The test of methyl bromide sorption discussed in Example 1 was repeated.

The test results show that the methyl bromide sorption rate of the EPS grape box made from non-lubed bead was 39% while the grape box made from lubed beads was 35%. The bead lubrication using polyethylene glycol and polyethylene wax decreased the methyl bromide sorption of the EPS grape boxes.

Example 3

Particle Coating II

NOVA D240B polystyrene raw beads were lubed using the following formulation and process:
D240B: 400 lbs
Drakeol 35 oil: 1500 ppm based on the weight of the D240B polystyrene beads.
Blend the above two materials for 20 minutes
Petrolite 5000 T6 polymer: 2500 ppm based on the weight of the D240B polystyrene beads.
Blend the above materials for another 20 minutes.

The pre-expansion and molding process of Example 1 was used to make EPS grape boxes. The test for methyl bromide sorption of Example 1 was repeated.

The test results show that the methyl bromide sorption rate of the EPS grape box made from non-lubed bead was 39% while the grape box made from lubed beads using mineral oil (Drakeol 35) was 34%. The beads lubricated with mineral oil and polyethylene wax decreased the methyl bromide sorption of the EPS grape boxes.

Example 4

Pre-Puff Coating

Ethylene-vinyl alcohol copolymer (EVOH, Soarnol E3808) alcohol solution was prepared according the following formulation:
E3808: 11 g
Water: 105 g
Isopropyl alcohol: 105 g NOVA R330B expandable polystyrene beads were pre-expanded in the Hirsch batch pre-expander to a density of 2.5 pounds per cubic foot (pcf). The pre-puff was then spray coated with the above prepared EVOH solution at a load level of 1500 ppm (solid EVOH weight) based on the weight of the pre-puff. The coated pre-puff was then rotated in a fiber class drum for 30 minutes. The coated and mixed pre-puff was aged for 24 hours before molding. EPS grape boxes were molded from aged pre-puff using the KG 606 or the Kurtz 812 molding machines. The dimensions of the grape box were 20×16×6.75 inches.

The test of methyl bromide sorption of Example 1 was repeated.

The test results show that the methyl bromide sorption rate of the EPS grape box made from non-coated pre-puff was 62% while the grape box made from coated pre-puff using EVOH solution was 56%. The pre-puff coating using the EVOH solution significantly decreased the methyl bromide sorption of the EPS grape boxes.

Example 5

Additives Added to Raw Bead Surface

Additives, such as mineral oil were added to the bead surface through the impregnation process. Specific amounts, i.e., 0.5 parts per hundred of the additives were charged to the impregnation reactor along with the standard formulations. The obtained beads were hot air expanded to about 25 pounds per cubic foot.

The pre-expansion and molding process of Example 1 was repeated to make EPS grape boxes, and the test of methyl bromide sorption of Example 1 was repeated.

The test results show that the methyl bromide sorption rate of the EPS grape box made from non-additive beads was 44% while the grape box made from beads with the above described additives and a pre-nucleation process was 32%. The bead additive and the pre-nucleation process substantially deceased the methyl bromide sorption of the EPS grape boxes.

While the present invention has been particularly set forth in terms of specific embodiments thereof, it will be evident to those skilled in the art that numerous variations and details of the invention may be made without departing from the instant invention as defined in the appended claims.

What is claimed is:

1. A method for improving the resistance of fumigant sorption in a produce container in a fumigation process, the steps comprising:
   making a produce container using the steps comprising
   pre-expanding expandable polymer particles having a density of from about 40 to about 32 pounds per cubic foot to form pre-expanded particles with a density ranging from about 12.0 pounds per cubic feet to 1.0 pounds per cubic feet to form pre-expanded particles;
   applying a coating to said pre-expanded particles, said coating comprised of a chemical selected from the group consisting of mineral oil, polyethylene wax, and polyethylene glycol in an amount ranging from about 0.05 to about 5.0 parts per hundred; and
   forming said produce container from said pre-expanded particles by injecting the pre-expanded particles into a mold having the shape of a produce container and heating the closed mold to further expand and fuse the pre-expanded particles to form said produce container;
   wherein the residual fumigant level of the produce container is not more than 5 ppm based on the weight of the produce container after the produce container has been introduced to a fumigant in a sealed chamber such that the concentration of the fumigant in the chamber is at least 48 ounces/1000 ft$^3$ for an initial 30 minutes and at least 38 ounces/1000 ft$^3$ for a subsequent 90 minutes and aeration air is subsequently exchanged for the fumigant in the chamber.

2. A method of claim 1, wherein said chemical is mineral oil.

3. A method of claim 1 wherein said polymer particles are polystyrene particles.

4. A method for improving the resistance of fumigant sorption in a produce container in a fumigation process, the steps comprising:
   making a produce container using the steps comprising
   applying to expandable polymer particles a coating comprised of a chemical selected from the group consisting of mineral oil, polyethylene wax, and polyethylene glycol in an amount ranging from about 0.05 to about 5.0 parts per hundred;

pre-expanding said expandable polymer particles having a density of from about 40 to about 32 pounds per cubic foot to form pre-expanded particles with a density ranging from about 12.0 to about 1.0 pounds per cubic feet to form pre-expanded particles; and forming said produce container from said pre-expanded particles by injecting the pre-expanded particles into a mold having the shape of a produce container and heating the closed mold to further expand and fuse the pre-expanded particles to form said produce container;

wherein the residual fumigant level of the produce container is not more than 5 ppm based on the weight of the produce container after the produce container has been introduced to a fumigant in a sealed chamber such that the concentration of the fumigant in the chamber is at least 48 ounces/1000 ft$^3$ for an initial 30 minutes and at least 38 ounces/1000 ft$^3$ for a subsequent 90 minutes and aeration air is subsequently exchanged for the fumigant in the chamber.

5. A method of claim 4, wherein said chemical is mineral oil.

6. A method of claim 4 wherein said polymer particles are polystyrene particles.

7. A method for improving the resistance of fumigant sorption in a produce container in a fumigation process, the steps comprising:

making a produce container using the steps comprising
increasing the cell size of expandable polymer particles; and
using said expandable polymer particles to mold said produce container by injecting the pre-expanded particles into a mold having the shape of a produce container and heating the closed mold to further expand and fuse the pre-expanded particles to form said produce container;

wherein the residual fumigant level of the produce container is not more than 5 ppm based on the weight of the produce container after the produce container has been introduced to a fumigant in a sealed chamber such that the concentration of the fumigant in the chamber is at least 48 ounces/1000 ft$^3$ for an initial 30 minutes and at least 38 ounces/1000 ft$^3$ for a subsequent 90 minutes and aeration air is subsequently exchanged for the fumigant in the chamber.

8. A method of claim 7 wherein said polymer particles are polystyrene particles.

9. The method according to claim 1, wherein the fumigant comprises methyl bromide.

10. The method according to claim 4, wherein the fumigant comprises methyl bromide.

11. The method according to claim 7, wherein the fumigant comprises methyl bromide.

* * * * *